(12) United States Patent
Xie et al.

(10) Patent No.: US 7,468,249 B2
(45) Date of Patent: Dec. 23, 2008

(54) DETECTION OF CHROMOSOMAL DISORDERS

(75) Inventors: Zhiyi Xie, Carlsbad, CA (US); Soonkap Hahn, San Clemente, CA (US); Tim Watanaskul, Oceanside, CA (US)

(73) Assignee: Biocept, Inc., San Diego, CA (US)

( * ) Notice: Subject to any disclaimer, the term of this patent is extended or adjusted under 35 U.S.C. 154(b) by 508 days.

(21) Appl. No.: 10/840,208

(22) Filed: May 5, 2004

(65) Prior Publication Data

US 2005/0250111 A1 Nov. 10, 2005

(51) Int. Cl.
C12Q 1/68 (2006.01)
(52) U.S. Cl. .......................................................... 435/6
(58) Field of Classification Search ................. None
See application file for complete search history.

(56) References Cited

U.S. PATENT DOCUMENTS

| | | | |
|---|---|---|---|
| 5,213,961 A | 5/1993 | Bunn et al. ................... 435/6 |
| 5,639,606 A | 6/1997 | Willey .......................... 435/6 |
| 5,643,765 A | 7/1997 | Willey ...................... 435/91.2 |
| 5,716,784 A | 2/1998 | Di Cesare .................... 435/6 |
| 5,888,740 A | 3/1999 | Han .............................. 435/6 |
| 5,994,057 A | 11/1999 | Mansfield ..................... 435/6 |
| 6,040,138 A * | 3/2000 | Lockhart et al. .............. 435/6 |
| 6,251,601 B1 * | 6/2001 | Bao et al. ...................... 435/6 |
| 6,268,147 B1 | 7/2001 | Beattie et al. ................. 435/6 |
| 6,319,674 B1 * | 11/2001 | Fulcrand et al. ............. 435/7.1 |
| 6,551,783 B1 | 4/2003 | Carey .......................... 435/6 |
| 2003/0054386 A1 * | 3/2003 | Antonarakis et al. ......... 435/6 |

FOREIGN PATENT DOCUMENTS

EP 0 639 647 A2 2/1995
EP 1329517 A1 * 7/2003

OTHER PUBLICATIONS

Markoulatos et al. ("Multiplex polymerase chain reaction: a practical approach" J Clin Lab Anal. 2002;16(1):47-51).*
Norman Arnheim, et al., Special Report, "Polymerase Chain Reaction", Oct. 1, 1990 C&EN, pp. 36-47.
Rahil Haissam et al: "Rapid Detection of Common Autosomal Aneuploidles By Quantitative Fluorescent PCR on Uncultured Amnlocytes", European Journal of Human Genetics: DJHG, Aug. 2002, vol. 10, No. 8, pp. 462-466, ISSN: 1018-4813.
Chizhikov V et al: "Microarray Analysis of Microbial Virulence Factors", Applied and Environmental Microbiology, Washington DC, vol. 67, No. 7, Jul. 2001, pp. 3258-3263, ISSN: 0099-2240.
Zimmermann B et al: "Novel Real-Time Quantitative PCR Test for Trisomy 21", Clinical Chemistry, American Association for Clinical Chemistry, vol. 48, No. 2, 2002, pp. 362-363. ISSN: 0009-9147.
Higuchi R G et al: "Production of Single-Stranded DNA Templates By Exonuclease Digestion Following the Polymerase Chain Reaction", Nucleic Acids Research, Oxford University Press, Surrey, GV, vol. 17, No. 19, Oct. 11, 1989, p. 5865, ISSN: 0305-1048.
Pollack J R et al: "Genome-Wide Analysis of DNA Copy-Number Changes Using cDNA Microarrays", Nature Genetics, Nature America, New York, vol. 23, No. 1, Sep. 1999, pp. 41-46, ISSN: 1061-4036.
Wells Dagan et al: "Cytogenetics in Reproductive Medicine: The Contribution of Comparative Genomic Hybridization (CGH)", Bioessays: News and Reviews in Molecualr, Cellular, and Developmental Biology, vol. 25, No. 3, Mar. 2003, pp. 289-300, ISSN: 0265-9247.
Armour J A L et al: "The Detection of Large Deletions or Duplications In Genomic DNA", Human Mutation, Nov. 2002, vol. 20, No. 5, pp. 325-337, ISSN: 1098-1004.

* cited by examiner

Primary Examiner—Kenneth R. Horlick
Assistant Examiner—Christopher M. Babic
(74) Attorney, Agent, or Firm—Fitch, Even, Tabin & Flannery

(57) ABSTRACT

Methods for detecting in a single assay any one of multiple chromosomal disorders that result from aneuploidy or certain mutations, particularly microdeletions, and kits for use therein. A polymerase chain reaction (PCR) is carried out to amplify eukaryotic genomic DNA using a plurality of primer oligonucleotide pairs wherein one primer of each pair has a detectable label attached 5' thereto. A plurality of the primer pairs are targeted to DNA segments of different chromosomes of interest which are indicative of potential chromosomal disorders, and one pair is targeted for a control gene. The amplified PCR products are purified, and single-stranded DNA having the detectable labels is obtained therefrom and hybridized with spots on a microarray that each contain DNA oligonucleotide probes having nucleotide sequences complementary to a nucleotide sequence of one strand of each segment. The microarray is imaged for presence of labels on its respective spots, and the absence or presence of chromosomal disorders as indicated by one or more of the targeted DNA segments of interest is diagnosed by first comparing the imaging results to the imaging of spots specific to the control gene and then to results obtained from imaging normal DNA.

11 Claims, No Drawings

DETECTION OF CHROMOSOMAL DISORDERS

FIELD OF THE INVENTION

The present invention relates to detecting aneuploidy and mutations, particularly microdeletions, by quantitatively comparing copy numbers indicative of whole chromosomes, and/or of chromosomes wherein a section may be missing or significantly mutated, in unknown samples and comparing the results with those of normal samples. More particularly, the invention relates to prenatal detection of fetal chromosomal disorders, such as aneuploidy, including trisomy 21 (Down's syndrome), trisomy 13, trisomy 18, and male and female sex chromosome abnormalities, and microdeletion syndromes, including Cri du chat syndrome, Williams-Beuren syndrome, and DiGeorge syndrome, and other like disorders.

BACKGROUND OF THE INVENTION

Aneuploidy is a common form of chromosome mutation wherein the number of individual chromosomes present in a cell increases or decreases from the number present in a normal cell. The absence of one chromosome from the diploid complement is referred to as monosomy, whereas the presence of an extra chromosome is referred to as trisomy. Trisomy 21 is a condition where an extra chromosome 21 exists and is the most common form of aneuploidy that gives rise to Down's syndrome, a congenital manifestation of potentially severe mental retardation.

Prenatal diagnosis of chromosomal disorders using karyotypes in combination with amniotic fluid or chorionic villus sampling has become the standard in highly developed countries worldwide in instances where indications are present. A karyotype is a collection of indices which characterize the state of a chromosomal complement; it includes total chromosome number, copy number of individual chromosome type and chromosome morphology. Karyotypes are determined by staining metaphase (or condensed) chromosomes. Metaphase chromosomes were used often because, until recently, it had not been possible to visualize interphase chromosomes because of their dispersed condition and the lack of sensitivity from such stainings. Metaphase chromosomes can be stained using a number of cytological techniques and reveal a longitudinal segmentation into entities generally referred to as bands. The banding pattern of each chromosome is unique and thus permits unambiguous chromosome identification including any abnormalities. Unfortunately, such analysis requires cell culturing and the preparation of high quality metaphase chromosomes, which may take 1-3 weeks.

Some attempts have been made to analyze chromosomes without cell culturing, and one such method is described in U.S. Pat. No. 5,447,841. A rapid partial karyotype analysis is obtained using fluorescence in situ hybridization (FISH) with respect to the chromosome-specific DNA targets which are present upon uncultured interphase amniotic cells. In this approach, fluorescently labeled probes are hybridized to complementary sites on chromosomes bound to a solid support. This approach overcomes a limitation of conventional cytological staining methods which results from a lack of stains that are sufficiently chromosome-specific; reagents comprising heterogeneous mixtures of labeled nucleic acid fragments are provided that can be hybridized to the DNA of specific chromosomes, specific subsets of chromosomes or specific subregions of specific chromosomes. Although the FISH method opens up the possibility of rapid and highly sensitive detection of chromosomal disorders in both metaphase and interphase cells, it is not without some shortcomings: 1) a number of chromosomal disorders related to microdeletions require still metaphase chromosomes due to the lack of their signal sensitivity and 2) the number of chromosomes which can be simultaneously diagnosed is limited to the resolution of the fluorescence microscope filters. Moreover, performance of the FISH method requires highly trained technicians and expensive equipment and reagents.

A method for quantitating cDNA species by PCR by coamplifying a second, unrelated template has been described, see Rappolee, D. A., et al., Science 241: 708-712 (1988). This method is critically dependent on certain variables, including cycle number and amount of starting mRNA of each species. Even when these variables are adequately controlled, it is unlikely that an unrelated control template will be amplified at precisely the same rate as the unknown template. Small differences in the rate of amplification of the two templates are magnified during PCR and may grossly over- or underestimate the amount of the unknown template present in the ultimate assay that is used.

It was reported in Amhelm, Norman et al. Polymerase Chain Reaction, *Chemical & Engineering News*, 36-47 (Oct. 1, 1990), that PCR has been used for the prenatal diagnosis of genetic diseases to analyze fetal DNA to determine whether it contains a mutated form of a gene that would cause the disease. Following PCR amplification, labeled probes are used to test a PCR sample for the presence of the disease causing allele. It is stated that the presence or absence of several different causing genes can be determined in a single sample. It is further indicated that PCR detection methods have employed reporters, based upon enzymes, chemiluminescence and fluorescence, in detection methods to find a pathogen using a dot blot format by spotting PCR-amplified product on a nylon membrane and then exposing that dot-carrying membrane to a single stranded DNA probe that will specifically anneal to the PCR product of interest, the probe being labeled radioactively or with molecules that are detectable by fluorescence or chemiluminescence. This procedure was limited to screening for one analyte at a time. Alternatively described is the use of PCR to label the pathogen-specific product itself by incorporating a label in the side chain of the nucleotides where it will not interfere with the ability of the primer to anneal to the target or to be extended by the polymerase. The incorporation of fluorescent dyes, such as fluorescein, or the vitamin biotin are mentioned, that might be attached by a short linker arm to the 5' end of the primer or to one of the bases within the primer sequence. It is then suggested that, once the appropriately labeled, amplified PCR product has been produced, it can be detected by "capturing" with a non-labeled pathogen-specific probe attached to a solid support. This alternative process was referred to as the reverse dot blot procedure when it was developed at Cetus Corporation. After washing to get rid of all excess labeled-primers or the like, the presence of the analyte is detected as by binding to the bacterial protein streptavidin and then treating with an enzyme. Another capture suggestion is to label one primer with a fluorescent dye and the other with biotin and then capture the double-stranded product with streptavidin and test for the fluorescence. It is mentioned that this capture approach will allow the simultaneous detection of different diagnostic sequences by using sets of primers for different specific pathogens one of which is labeled. It is suggested that the total PCR product is hybridized to a suitable nylon membrane support having distinct regions, each with a capture probe that is specific for the PCR product of one of the pathogens. Then, the support is stringently washed following hybridizing and if the label was biotin, the addition of the strepavidin-enzyme complex followed by the appropriate enzyme substrate would indicate the presence of any one of the pathogens by color production in that specific region. It is suggested that this procedure might be preferred over the original dot blot procedure which would involve many more manipulations because it would require that a different aliquot of the unlabeled PCR product be tested with each labeled, pathogen-specific probe in a separate hybridization experiment.

U.S. Pat. No. 5,213,961 to Bunn et al. discloses a method of quantitative PCR by competitive methodology, wherein the parameters affecting DNA amplification and a mechanism to distinguish differences in template (both test and control) ratios and copy numbers are discussed. It is mentioned that it might be used to detect somatic cell mutations. Bunn et al. address the effect of various parameters on the amplification process which arise predominantly from the nature of the DNA primers and their respective primer binding sites; however, the system is limited to use of a standard that is sufficiently close to the target that the target and sample are co-amplified at the same rate by PCR. Moreover, the standard must differ from the target such that its length can be later altered by enzymatic action, thus allowing the standard and target to be separated and quantified by electrophoresis.

PCT published application WO 94/03638 discloses a different method where aneuploidy is detected by utilization of short tandem repeat DNA sequences present in chromosome DNA, with PCR methodology being utilized to amplify the short tandem repeat sequences.

U.S. Pat. No. 5,888,740 to Han uses DNA templates engineered as internal controls during PCR reactions for the quantitative measurement of genomic DNA levels. These control DNA templates are designed to have the same sequences of primers for PCR reaction as the test sample DNA templates. The goal is for amplification to proceed at the same rate, thereby providing control of the amplification rate. However, this method requires a specific internal control for each chromosome, which is complex. In addition, the PCR reaction for each chromosome must be carried out in a separate well of a microtiter plate or other container.

U.S. Pat. No. 6,551,783 to Carey teaches a method of quantitation of expression of two target genes in a simultaneous PCR based assay which employs a system where a fluorescent marker or reporter probe is displaced from the strand of DNA being amplified in a manner in which the fluorescent probe escapes from the vicinity of a quencher dye. By using two different fluorescent probes, PCR multiplexing of two genes are simultaneously effected. One target gene is a ubiquitously expressed marker gene, such as GAPDH or DAD-1. The method taught is limited to one unknown target at a time.

Another method, described in WO94/23023, quantifies a target gene based on multiplex PCR for the target gene, a housekeeping gene and their competitive templates with mutations, such as point mutations, insertions or deletions. This method is complex and cumbersome, employing gel electrophoresis in the final analysis.

None of the aforementioned methods of screening for chromosomal disorders is felt to be totally satisfactory to screen for multiple disorders simultaneously, so the search has continued for a comprehensive screening procedure that is easy to use and provides rapid results.

SUMMARY OF THE INVENTION

The present invention uses a combination of multiplex PCR of genomic DNAs and a quantifiable microarray platform for hybridization with the PCR products to overcome shortcomings of previous methods by offering: 1) comprehensive screenings covering aneuploids and mutations, particularly microdeletions, simultaneously; 2) fast results within 24-48 hours; and (3) ease in use. The use of rule-based diagnostic algorithms to interpret the imaging pattern of the microarray enhances the accuracy of the quantified results. The present invention provides kits and methods for fast, accurate, simple and inexpensive detection of chromosomal disorders, which can be used for the simultaneous detection of aneuploidy (including trisomy 21, trisomy 13, trisomy 18, and sex chromosome, e.g. chromosome X, abnormalities) and microdeletions, including Williams-Beuren syndrome, Cri du chat syndrome, Di George syndrome, Pradar-Willi syndrome and Angelman syndrome (both of which involve deletions of part of chromosome 15), Kallman's syndrome, and steroid sulfatase syndrome.

The present invention more specifically provides kits and methods for prenatal detection of Down's syndrome and other aneuploidies and chromosomal disorders using PCR, hybridization to chromosome-specific probes, and diagnosis. The results of diagnosis are enhanced through the use of rule-based algorithms.

In one particular aspect, the invention provides a method for detecting any one of multiple chromosomal disorders in a single assay, which method comprises the steps of (a) making a polymerase chain reaction (PCR) mixture by mixing in a vessel components comprising (i) eukaryotic genomic DNA; (ii) a plurality of pairs of forward and reverse DNA primer oligonucleotides wherein one primer of each said pair is complementary to a 3' sequence of a targeted segment of a first DNA strand of the eukaryotic DNA and the other primer is complementary to the 3' sequence of the second strand of the targeted segment, the length of the segment of eukaryotic DNA being between about 50 and about 300 base pairs, wherein one of the primers of each pair has a detectable label attached to its 5' end, and wherein a plurality of the pairs of primers are each targeted to a segment of a selected different chromosome of interest which is indicative of a potential chromosomal disorder and one pair is targeted for a segment of a control gene, and (iii) PCR buffers and enzymes necessary to carry out PCR amplification, (b) conducting a PCR for between about 5 and about 60 temperature cycles to create amplified PCR products, (c) purifying said products of step (b) and obtaining single-stranded DNA having the detectable labels, (d) contacting a microarray with products of step (c), which microarray has a plurality of spots that each contain DNA oligonucleotide probes having nucleotide sequences complementary to a nucleotide sequence of one of said strands of each of said targeted segments, (e) hybridizing said DNA oligonucleotide probes and said PCR-amplified label-containing single-stranded products, (f) detecting the presence and relative quantity of the PCR-amplified products hybridized to the microarray by imaging the microarray, and (g) diagnosing whether or not a chromosomal disorder exists with respect to one or more of said selected different chromosomes by comparing said imaging of the relevant spots on said microarray for each said targeted segment of a selected chromosome to the imaging of spots relevant to said control gene and then to results obtained from similar testing of genomic DNA known to be normal.

In another particular aspect, the invention provides a kit to detect chromosomal disorders, which kit comprises a kit to detect chromosomal disorders, which kit comprises (a) a plurality of pairs of DNA oligonucleotides that will function as primers in a polymerase chain reaction (PCR) for amplifying mammalian genomic DNA, wherein one primer of each pair of oligonucleotides is complementary to a 3 nucleotide sequence of a first strand of a targeted segment of mammalian genomic DNA and the other primer of each pair of oligonucleotides is complementary to the 3 nucleotide sequence of the second strand of the targeted DNA segment, one said primer of each pair having a detectable label covalently linked to the 5 end thereof; a plurality of said pairs of DNA primers being targeted to amplify segments of selected different chromosomes of interest which are indicative of potential chromosomal disorders, and one said pair being targeted to amplify a segment of a control gene; (b) buffers and enzymes for carrying out (i) a PCR, (ii) DNA—DNA hybridization and washing, and (iii) colorimetric quantitation; (c) at least one microarray having a plurality of spots, at least one of which spots has attached thereto DNA sequences complementary to the label-bearing amplified strand of each respective targeted genomic DNA segment; and (d) means for diagnosis for chromosomal disorders using intensity imaging results from hybridization reactions between PCR amplification products and the respective spots on the microarray, which means utilizes imaging results from similar testing of normal genomic DNA.

In a further particular aspect, the invention provides a method for detecting any one of multiple chromosomal disorders in a single assay, which method comprises the steps of: (a) making a polymerase chain reaction (PCR) mixture by mixing in a vessel components comprising: (i) eukaryotic genomic DNA; (ii) a plurality of pairs of forward and reverse DNA primer oligonucleotides wherein one primer of each said pair is complementary to a 3 sequence of a targeted segment of a first eukaryotic DNA strand and the other primer is complementary to the 3 sequence of the second strand of the target segment, the length of the segment of eukaryotic DNA being between about 100 and about 250 base pairs, wherein one of the primers of each pair has a color-detectable label attached at the 5 end thereof, and wherein a plurality of the pairs of primers are targeted to segments of selected different chromosomes of interest which are indicative of potential chromosomal disorders and one pair is targeted for a segment of a control gene; and (iii) PCR buffers and enzymes necessary to carry out PCR amplification; (b) conducting a PCR for between about 5 and about 60 temperature cycles to create amplified PCR products; (c) purifying said products of step (b) and obtaining single-stranded DNA having the color-detectable labels by digestion of one strand of the amplified double-stranded PCR product, (d) contacting a microarray with products of step (c), which microarray has a plurality of spots that each contain DNA oligonucleotide probes having nucleotide sequences complementary to a nucleotide sequence of one of said strands of said targeted segments; (e) hybridizing said DNA oligonucleotide probes and said PCR-amplified label-containing single-stranded products; (f) detecting the presence and relative quantity of the PCR-amplified products hybridized to the microarray by colorimetric imaging of the microarray; and (g) diagnosing whether or not a chromosomal disorder exists with respect to one or more of said different chromosomes of interest by first comparing said imaging of a relevant spot on said microarray for each said chromosome of interest to the imaging of a spot relevant to said control gene to obtain an I-ratio; then comparing each I-ratio to N-ratios that have been obtained as a result of similar testing of genomic DNA known to be normal.

DETAILED DESCRIPTION OF THE PREFERRED EMBODIMENTS

As indicated generally above, the invention facilitates detection of chromosome aneuploidy, including trisomy 21, 18, 13 and sex chromosome abnormalities, which are sometimes referred to as gene dose abnormalities or aberrations. At the same time, chromosomal mutations, particularly those which are in the form of the deletion of a portion of a gene sequence that results in one of the various disorders called microdeletion syndromes, can be detected by selecting target sequences within or encompassing the affected gene region (i.e., the deletion region) and comparing the gene doses indicative of the region where such deletion would occur versus an internal control and normal DNA. Examples of some such chromosome microdeletion syndromes and deletion regions to be targeted include: Prader-Willi and Angelman syndrome (deletion site 15q11-q13), William-Beuren syndrome (deletion site 7q11.23), Cri du chat syndrome (deletion site 5p), Kallman syndrome (deletion site Xp22.3), Di George syndrome (deletion site 22q 11.2), Duchenne/Becker syndrome (deletion site Xp21), and Steroid sulfatase deficiency (deletion site Xp22). Some comparisons are best made versus normal DNA of a subject of the same gender.

The following definitions of terms and acronyms are provided to better understand the detailed description set forth hereinafter.

Chromosomal disorder is meant to include any gross abnormality in a chromosome or the number of chromosomes. For example, this includes detecting trisomy in chromosome 21, aberrations in the X- and Y-chromosomes, and the detection of mutations such as deletions, insertions and/or alterations in individual genes.

Hybridization is used in this application to denote the formation of a duplex structure between complementary strands of DNA where one of the two strands is preferably immobilized onto a solid surface or matrix.

Annealing is used herein to mean incubation of a single-stranded or heat-denatured duplex nucleic acid analyte with an oligonucleotide probe or primer, under hybridization conditions enabling the probe or primer to bind to its complementary sequence within the analyte nucleic acid, either at a slowly decreasing temperature or at a single temperature.

Analyte or analyte nucleic acid is used to describe a compound in a DNA sample which is the object of analysis.

Label or detectable label (or "tag") refers to a substituent that can be attached to a nucleic acid sequence which enables its detection and/or quantitation. Examples include radiolabels such as $^{32}P$, $^{33}P$, and $^{35}S$; colorimetric indicators, such as fluorescent, chemiluminescent or colored compounds; ligands such as biotin; and chemical groups that are distinguishable by mass or other spectroscopic properties. More specific examples of suitable labels include xanthine dyes, rhodamine dyes, naphthylamines, benzoxadiazoles, stilbenes, pyrenes, acridines, Cyanine 3 and Cyanine 5. A label is preferably introduced into analyte nucleic acid by incorporation directly as a part of a primer although indirect addition by chemical reaction, enzymatic reaction, or hybridization or annealing of a label with an intermediate ligand may be used.

Probe refers to a nucleic acid sequence used as a reagent to bind its complementary sequence in an analyte nucleic acid via a hybridization reaction. Capture probe may be used herein to mean a probe bound at one end (i.e. tethered) to a solid surface, enabling the capture of a nucleic acid or oligonucleotide containing a complementary sequence onto the solid surface in a hybridization reaction.

Sequence means a string of bases within a nucleic acid comprising A, G, C, T residues in DNA, linked together in a specific order and chain length.

Complementary or complementary sequence refers to two sequences that are capable of forming a two-stranded (duplex) structure under stringent conditions.

Target, target sequence, target strand or target nucleic acid is used herein to refer to a nucleic acid sequence the presence of which is the object of detection, for example, through hybridization with a specific DNA probe. The term "targeted" is sometimes used in a broad sense to mean the selection of a particular nucleic acid segment of a chromosome.

Tethered, or surface-tethered is used herein to refer an oligonucleotide DNA probe that is bound at one end with some surface, through a covalent bond or other strong bond formed between a functional group on the surface and a functional group at one end of the DNA probe.

Solid phase hybridization means a hybridization reaction conducted in which one of the two "reactant strands" participating in formation of a duplex structure is tethered or otherwise immobilized on a solid support.

Flanking or bordering is used to refer to nucleic acid segments that are near, adjacent to and/or include the ends of a targeted DNA segment of a chromosome.

Oligonucleotide means a short DNA strand, which can be chemically synthesized, typically of a length up to about 100 nucleotides.

Gene means a unit of genetic function, including sequences encoding a protein, intronic (noncoding) sequences interpersed within a gene, and additional sequences functioning in the regulation of the gene.

Microarray or DNA chip means a two-dimensional or three-dimensional (3D) array of surface-tethered DNA probes formed on a surface or on microspots that are affixed to a surface, enabling simultaneous analysis of a multiplicity of hybridization reactions, typically in a miniaturized format, with individual DNA probes arrayed at center-to-center spacing of less than one millimeter.

Primer means an oligonucleotide possessing a free 3'-OH terminus, which will base-pair with a "template strand" and thus can be elongated by a polymerase enzyme. For example, an oligonucleotide primer annealed with a DNA template can serve as a substrate (along with deoxynucleoside 5'-triphosphates) for a DNA polymerase, resulting in "primer extension," as in the PCR reaction.

Primer pair means two primers that bind to opposite strands of a targeted nucleic acid segment.

PCR fragment means a fragment of DNA of defined length (defined by the spacing between priming sites on the template) formed by the polymerase chain reaction.

Denature or denatured means separation (dissociation) of the two strands of a duplex nucleic acid molecule under conditions which destabilize the double helix, most commonly, elevation of temperature ("heat-denaturation").

5'-end/terminus means the end of a nucleic acid chain containing a nucleotide with a non-esterified carbon-5 on its deoxyribose.

3'-end/terminus means the end of a nucleic acid chain containing a nucleotide with a non-esterified carbon-3 on its deoxyribose.

PCR—polymerase chain reaction.

SSC—saline sodium citrate, a solution containing 150 mM sodium chloride and 15 mM sodium citrate.

Applicant's diagnostic method utilizes PCR to initially amplify specific DNA sequences that are present in low abundance relative to the total DNA. By using PCR, a specific DNA sequence can be amplified one hundred thousand fold or more to facilitate its detection it is when present in the starting DNA.

U.S. Pat. Nos. 4,683,202, 4,683,195, 4,800,159 and 4,965,188, the disclosures of which are incorporated herein by reference, provide details of the now well known PCR process which is utilized by the present invention. PCR amplifies a DNA sequence several orders of magnitude in a few hours through the use of oligonucleotide primers complementary to sequences flanking a particular region of interest to effect primer-directed DNA synthesis in opposite and overlapping directions. Knowledge of such flanking sequences is used to design two synthetic, single-stranded olignucleotides, usually about 20 nucelotides in length, that will serve as primers. The sequence of each of these primers is chosen so that it has base pair complentarity with its respective flanking sequence that has been selected. PCR begins by denaturing the double-stranded target DNA, followed by annealing the primers (one for each strand) to the sequences flanking the target analyte. Each primer forms a duplex with one flanking sequence so that the 3 hydroxyl end of the primer faces the target analyte sequence. Addition of a DNA polymerase and deoxynucleoside triphosphates causes a new DNA strand to form, beginning at the primer and extending across the target sequence, thereby making a copy of the target. These steps, i.e. DNA denaturation, primer annealing, and DNA polymerase extension, represent one PCR cycle; each step is carried out at an appropriate temperature. The extension product will generally extend to and include the sequence complementary to the primer at the other end of the target sequence. Thus, each new extension product then acts as a template for the next cycle following denaturation.

By employing repeated cycles of high temperature template denaturation, oligonucleotide primer reannealing, and polymerase-mediated extension, DNA sequences can be faithfully amplified several hundred-thousand fold. Generally PCR requires knowledge of the sequence of both the 5' and the 3' end of the template or segment being amplified so that two different primers for each template may be designed, one forward primer for the sense strand and one reverse primer for the antisense strand.

The PCR process in the present invention uses a plurality of pairs of primers that include different oligonucleotides that are capable of acting as points of initiation of DNA synthesis of desired DNA segments of interest. Each of them is complementary to one of the two 3' borders of the duplex segment desired to be amplified; they are often referred to as forward and reverse primers. The forward primers are directed from the 5' region toward the 3' region of the gene (i.e. they are complementary to the noncoding or antisense strand), and the reverse primers are directed from the 3' region toward the 5' region of the gene (i.e., they are complementary to the coding or sense strand). The primers are combined with the other PCR reagents under conditions that induce primer extension, i.e., with four different deoxyribonucleoside triphosphates (or analogues thereof), an appropriate polymerase and an appropriate buffer ("buffer" includes agents to effect desired pH and ionic strength, etc.) and maintained at a suitable temperature. In a PCR method where the polymerase is Taq polymerase or an equivalent polymerase, the buffer may contain 1.5-2 mM of a magnesium salt, preferably $MgCl_2$, 15-200 μM of each nucleoside triphosphate, 1 M of each primer and e.g. 50 mM KCl, 10 mM Tris buffer at pH 8.4, and 100 μg/ml gelatin. Such kits for performing PCR amplification are commercially available from numerous vendors.

Suitable oligonucleotide primers for the detection of human chromosomal disorders can be readily designed using currently available sequence information and standard techniques known in the art for the design and optimization of primer sequences. Oligonucleotides may be synthesized by standard methods known in the art, e.g., by use of an automated DNA synthesizer such as one of those commercially available from Biosearch (Novato, Calif.); Applied Biosystems (Foster City, Calif.) and others. The primers used herein are of sufficient length to specifically hybridize to one strand at selected flanking sites which are contiguous to a DNA segment of a chromosome that will be indicative of the disorder of particular interest. Such DNA segment lengths may include as few as 14, 15, 16, 17, 18 or 19 base pairs; however, often they will usually include 20, 30, 40, 50, 60, 70, 80, 90 or 100 or more nucleotides. Often the DNA segment to be amplified will be between 100 and 250 nucleotide base pairs (bp); however, it may be desired to amplify segments between 50 and 300 bp, e.g., when analyzing for aneuploidy. The lengths of the probes and primers that may be short as 14, 15, 16, 17, 18 or 19 nucleotides, but they will usually contain at least 20, 30, 40, or 50 or nucleotides or even more.

Each primer should be sufficiently long to initiate or prime the synthesis of extension DNA products in the presence of an appropriate polymerase and other reagents, such as those mentioned above. Appropriate primer length is dependent on many factors, as is well known; typically, in the practice of the present method, the primers that are used usually contain about 15-40 nucleotide residues. Relatively short primer molecules generally require lower reaction temperatures to form and to maintain the primer-template complexes that support the chain extension reaction.

The primers which are used need to be substantially complementary to a nucleic acid containing the selected sequences to be amplified, i.e., the primers must bind to, i.e. hybridize with, nucleic acid containing the selected sequence (or its complement). Although the primer sequence need not entirely be an exact complement of the template; for example, a non-complementary nucleotide fragment or other moiety may be attached to the 5' end of a primer. However, the remainder of the primer sequence is preferably complementary to the selected nucleic acid sequence, and such are typically used.

Generally, any specific nucleic acid sequence can be amplified by the PCR process so long as a sufficient number of bases at both ends of the sequence are known in sufficient detail so that two oligonucleotide primers can be prepared which will hybridize to different strands of the desired sequence that are located at the desired relative positions along the nucleic acid sequence. As a result, the extension product synthesized from one primer, following its separation from its template (complement), will then serve as a template for extension of the other primer into a nucleic acid of defined length in the next cycle.

In a preferred embodiment of the present invention, primers are used in pairs. One of the primers, i.e., the forward primer, is complementary to a sequence at the 3' end of the antisense of a targeted DNA segment; the sequence is near, abuts and/or includes the 3' end of the antisense strand of the targeted segment. The other primer, i.e., the reverse primer, is the complement of a sequence at 3' end of the sense or coding strand of the targeted DNA segment; it includes, abuts and/or is near the 3' end of the sense strand of the targeted segment.

The primers are preferably between about 15 and about 40 nucleotides in length and more preferably between about 18 and about 35 nucleotides in length. The probes, which are attached or tethered to spots on a microarray, are preferably between about 25 and about 60 nucleotides in length and more preferably between about 35 and about 50 nucleotides in length. The probe sequences for capturing the labeled product should comprise enough nucleotides to allow hybridization under moderately stringent hybridization conditions. Although the probes can be attached to the surface of a flat substrate as a 2D array, a 3D array is preferred as mentioned hereinafter.

Human DNA, such as fetal DNA, often prenatal DNA obtained from amniotic fluid or possibly obtained from maternal blood, is suitably purified using a commercial DNA purification kit of the type available from many vendors. The concentration of the eukaryotic genomic DNA is assessed using a fluorimeter and PicoGreen dye as a staining agent. Alternatively, DNA can be extracted from fetal cells by standard DNA extraction techniques, the cells having been obtained by a suitable procedure such as amniocentesis. After appropriate dilution, an aliquot of the purified fetal DNA is added to a PCR reaction tube. In the preferred embodiment of the present invention, the added reaction components include appropriate concentrations of enzymes and buffers, including agents for maintaining desired pH and ionic strength, and other reactions conditions plus appropriate quantities of deoxyribonucleoside triphosphates.

The set of primers is selected so as to be specific to sections or segment of specific chromosomes that will be indicative of a disorder of interest. For example, it may be desired to quantitatively compare the copy numbers of whole chromosomes that are present. Alternatively, it may be desired to determine whether there may be a small section of a chromosome that is missing compared with a normal chromosome. To achieve this end, primers are appropriately selected that will flank a targeted region that will be indicative of the condition being analyzed. In addition, the overall set of primers will include one pair that is designed to amplify a control gene. The control gene is one which is present in human eukaryotic DNA and preferably one that is ubiquitously expressed and which is present on a chromosome other than where there is a targeted segment that is being used to diagnose a disorder. One preferred gene is glyceraldehyde-3-phosphate dehydrogenase (GAPD) which is found on chromosome 12.

Suitable forward and reverse primers and probes for the control gene GAPD and examples of pairs of primers that may be used to diagnose for five illustrative chromosomal disorders of aneuploidy are set forth hereinafter.

For GAPD, the primers may have the following oligonucleotide sequences: SEQ ID NOS: 1 and 2. The corresponding probe sequence may include the sequence: SEQ. ID NO: 19.

For Turner or Triple X disorder with respect to an abnormal number of X chromosomes in a female or for Klinefelter Syndrome where a male has more than one X chromosome, a pair of forward and reverse primers may be used to produce a 158 bp PCR fragment which includes the Xp22 region. The primers may have the sequences: SEQ ID NOS: 3 and 4. The corresponding probe may include the sequence: SEQ. ID NO: 20.

To distinguish between male and female and to diagnose for some rare cases of Klinefelter Syndrome, a pair of primers are used to produce a 148 bp PCR fragment related to the SRY gene on the Y-chromosome, which are: SEQ ID NOS: 5 and 6. The corresponding probe may include the sequence: SEQ. ID NO: 21.

A pair of primers designed to diagnose for Patau Syndrome, i.e., Trisomy 13, which result in the production of a 127 bp PCR fragment related to the ATP7B gene, are: SEQ ID NOS: 7 and 8. The corresponding probe may include the sequence: SEQ. ID NO: 22.

A pair of primers designed to diagnose for Edwards Syndrome, i.e., Trisomy 18, which result in the production of a 154 bp PCR fragment relative to the WDR7 gene, are: SEQ ID NOS: 9 and 10. The corresponding probe may include the sequence: SEQ. ID NO: 23.

A pair of primers designed to diagnose for Down's syndrome or Trisomy 21, which result in the production of a 124 bp PCR fragment relative to the SOD1 gene; are: SEQ ID NOS: 11 and 12. The corresponding probe sequence may include the sequence: SEQ. ID NO: 24.

Set forth hereinafter are examples of certain pairs of primers that are designed to analyze for microdeletions in a human chromosome.

For Cri du chat syndrome, a suitable pair of primers, that may be used to create a 167 bp PCR fragment targeted to a region of the TAS2R1 gene where the potential deletion site on chromosome 5 would appear, are: SEQ ID NOS: 13 and 14. The corresponding probe may include the sequence: SEQ. ID NO: 25.

For Williams-Beuren syndrome, a suitable pair of primers, that may be used to create a 138 bp PCR fragment targeted to a region of the ELN gene where the potential deletion site on chromosome 7 would appear, are: SEQ ID NOS: 15 and 16. The corresponding probe may include the sequence: SEQ. ID NO: 26.

For DiGeorge syndrome, a pair of primers, that may be used to create a 145 bp PCR fragment targeted to a region of the DGCR2 gene where the potential deletion site on chromosome 22 would appear, are: SEQ ID NO: 17 and 18. The corresponding probe may include the sequence: SEQ. ID NO: 27.

Although the foregoing sets of forward and reverse primers and corresponding probes are considered to be satisfactory for use in assays embodying various features of the invention, since the initial work was carried out, three now preferred sets of primers and corresponding probes have been developed to diagnose for three of these abnormalities, and one set has been developed to assay for Patau Syndrome (Trisomy 13) using a different marker, i.e., the FGF9 gene. This group of primers and probes is preferred when there is only a minimal amount of DNA available for the assay. These four sets of primers and probes are set forth hereinbelow and are used to assay for abnormalities on the following four genes: SRY, FGF9, WDR7 and SOD1. These four sets are presently preferred for diagnosing the respective disorders.

For SRY: primers SEQ ID NOS: 28 and 29; and probe SEQ ID NO: 36. These primers produce a 175 bp PCR fragment.

For FGF9: primers SEQ ID NOS: 30 and 31; and probe SEQ ID NO: 37. These primers produce a 139 bp PCR fragment.

For WDR7: primers SEQ ID NOS: 32 and 33; and probe SEQ ID NO: 38. These primers produce a 172 bp base PCR fragment.

For SOD1: primers SEQ ID NO: 34 and 35; and probe SEQ ID NO: 39. These primers produce a 129 bp PCR fragment.

Another set of primers and probe have been developed for substitution for those targeting the ATP7B gene on chromosome 13 which instead target the FGF9 gene. This set may be preferred when at least about 10 ng of DNA is available for the assay and consist of primers SEQ ID NOS: 40 and 41 and probe SEQ ID NO: 42.

To facilitate the assay, a kit is provided which includes all of the necessary tools. For example, a kit to detect multiple chromosomal disorders should contain:

(a) a plurality of pairs of DNA oligonucleotides that will function as forward and reverse primers in a polymerase chain reaction for amplifying mammalian genomic DNA, (these primers are designed to amplify targeted DNA segments of different mammalian chromosomes of interest which are indicative of potential chromosomal disorders, with one pair being targeted to amplify a control gene); one primer of each pair having a detectable label covalently linked to the 5' end thereof;

(b) buffers and enzymes for carrying out (i) a PCR, (ii) DNA-DNA hybridization and washing, and (iii) colorimetric quantization;

(c) at least one microarray (and preferably two duplicate microarrays) having a plurality of spots, at least one of which spots has attached thereto DNA probe sequences complementary to the label-bearing amplified strand of each respective targeted genomic DNA segment; and (d) means for diagnosis for chromosomal disorders using intensity imaging results from hybridization reactions between PCR amplification products and the respective spots on the microarray, which means utilizes imaging results from similar testing of normal genomic DNA.

The microarray has a plurality of microspots which have DNA probes attached thereto; these probes are each complementary to one of the labeled strands of amplified DNA. Although any of the myriad of developed arrays for labeled DNA targets can be used, including those two-dimensional assays wherein probes for targets are bound directly to a flat substrate or in a well of microtiter plate, it is preferred to provide a three-dimensional biochip, such as those described in U.S. Pat. No. 6,174,683 and in published international application WO 02/059372, entitled "Three Dimensional Format Biochips." In such a three-dimensional array, the probes are not connected to the solid surface of a well in a plate or to a glass slide or other flat plate, but they are instead presented in three-dimensional array by attachment to microspots of polymerized hydrogel. This arrangement isolates the probes from the solid substrate and presents an expanded surface area for presentation of the probes and for the ultimate capture of the labeled molecules. Preferably, a plurality of such 3D microspots are provided on each glass slide or in each well of a microwell plate, for each of the different targets employed in the assay.

The items other than the primer sets and the microarrays that are supplied as a part of the categorized portion of the kit are well known items which are commercially available and commonly included as part of any PCR kit. They are described in detail in the group of four U.S. references mentioned above which provide details of the now well known PCR process. As above-mentioned, the kit also includes appropriate chemicals to facilitate the hybridization reaction. Following incubation of the hybridization solution with the slides or wells, washing is carried out to remove unbound labeled target material so that the resulting slide can be observed in any suitable manner, as by using a fluorescence detector when fluorescent dyes are used or some other appropriate detectors depending on the nature of the particular label chosen for the kit. An appropriate algorithm is provided in the kit that is then used to interpret the results of the calorimetric scanning of the microarray; such is developed and based upon data earlier generated from control samples.

As an example of an assay procedure having various features of the invention that might be employed to detect any one of multiple chromosomal disorders resulting from aneuploidy or microdeletions, a small amount of an eurkaryotic genomic DNA is first obtained. It may be obtained from a fetal source or otherwise; frequently, the assay will be used to analyze genomic DNA obtained from amniotic fluid. At least about 0.1 nanogram of the genomic DNA is considered sufficient; however, as much as 10 ng may be used when such an amount is available. The DNA would be routinely purified using a purification kit such as are commercially available. Following purification, the concentration and purity are appropriately assessed, and upon obtaining a positive indication of purity and concentration, a multiplex PCR reaction is carried out.

A reaction chamber having a volume of about 50 microliters may be employed into which the ingredients of a commercially available PCR system are added along with a set of a plurality of pairs of primers which are designed to flank targeted regions of the various chromosomes that will be indicative of a potential disorder that is desired to be investigated. These pairs of primers are of course coordinated with probes that will be linked to spots on a microarray that will be provided as part of an assay kit. The probes, for instances where microdeletions are being investigated, will be designed to preferably bind to a segment of the normal antisense strand in the region where a potential deletion will occur and will thus be indicative of the occurrence of such a microdeletion when the intensity measured at that probe is substantially lower. Any number of pairs of such primers can be included, for example, even 100 or more such pairs. However, it will be more usual to include some 5 to 25 different pairs as a part of single kit. In addition to such a plurality of pairs of primers selected as indicative of chromosomal disorders of interest, one pair of primers which is specific to a selected control gene is also included. Each pair of primers is preferably selected to bind to locations on the chromosome that will result in amplification of a DNA sequence that will range between about 50 and 300 base pairs, more preferably between about 100 bp and 250 bp and most preferably between about 120 bp and 200 bp. About 1 µM each of forward and reverse primer is provided. Of course, the commercial PCR system kit includes appropriate amounts of deoxyribonucleoside substrates, appropriate enzymes, such as Taq, preferably hot-start capable polymerase, and buffers.

One of the primers of each pair is labeled, and the other primer of the pair is derivatized with 5'-phosphate. In the preferred embodiment, the forward primers are 5' phosphorylated, and the reverse primers are covalently bonded to a detectable label. Although as indicated hereinbefore in the definitions, there are a wide variety of detectable labels that may be included, preferably, colorimetric labels are employed, and more preferably, a fluorescent label such as a cyanine, is employed.

Generally between about 5 and 60 temperature cycles of the PCR replication process are carried out; often about 20-30 cycles will be sufficient to create the desired amount of the various amplified nucleic acid sequences to facilitate the investigation being carried out. Upon completion of the PCR amplification, the double-stranded products are purified using a standard procedure, such as column purification, e.g., designed to retain molecules having the size of 100 base pairs or greater. Commercial kits are available to facilitate such purification.

Following purification, the sense strand of the purified material is digested using a suitable exonuclease for that purpose; as a result of this step, the single-stranded products of the PCR amplification are obtained. Following digestion, the digested mixture is suitably diluted with a hybridization buffer. The resulting solution is heated for about 5 to 10 minutes to a temperature of about 95° C. to inactivate the exonuclease and to denature the single-stranded products. The resulting labeled antisense strands are dissolved in a hybridization solution which is preferably split into two equal parts that a pair of duplicate microarrays can be employed in parallel. Hybridization to each microarray is carried out in this solution which contains suitable buffers, for a period of about 10 to 20 hours, preferably for about 14 to 16 hours, at an appropriate temperature, such as 45° C. Following hybridization, each microarray is washed multiple times using a suitable buffer-containing solution and then subjected to fluorescent imaging with a laser scanner or some comparable device. Of course, if a different type of colorimetric label were employed, or if a radioactive or some other category of known label was instead used, an appropriate scanner/detector would be instead used.

Because the preferred assay procedure digests the sense strands of the amplified double-stranded PCR product, the microarrays are provided with probes that are selected segments of the sense strands of each of the stretches of nucleic acid being investigated and an appropriate segment of the sense strand of the selected control gene. Examples of corresponding probes for use with the pairs of primers disclosed were set forth hereinbefore. Generally, the probes range from about 25 to about 60 nucleotides in length. After the duplicate microassays are run in parallel, the fluorescent intensities of the probes on each of the microarrays are recorded, and these imaging results are then used for diagnosis, employing rule-based algorithms.

The signal intensity of each probe is initially normalized by dividing the recorded value by the signal intensity of the internal standard, for example, the signal intensity at the spot having the probe that is a segment of the sense strand of the GAPD gene on chromosome 12. This initial calculation produces a value for each probe in the form of a ratio against the selected internal standard, which is referred to as its I-ratio.

The I-ratios obtained for the same probes on each of the two duplicate slides are then compared. If there is a variation in these ratios for a particular probe between the duplicate slides of greater than 30% for the X and Y chromosomes, those values are felt to be potentially unreliable and thus are excluded from further calculations. Similarly, if the variation in the I-ratios for a particular probe for a targeted segment on some other chromosome is greater than 20%, this particular probe is likewise excluded from further calculations and analysis. For those that remain following such exclusion, the two I-factors are averaged, and this value is thereafter used.

To provide the basis for analysis of the results obtained from such an unknown sample, sets of DNA that are known to be normal are first run, and these results are used to determine normal ratios with respect to each of the selected DNA sequences. For example, 12 normal male samples are run, and with respect to each sample, the ratio for each probe against the internal standard (which was here selected as the GAPD gene) is calculated. These 12 ratios are then averaged to provide "normal ratios" (N-ratios) expected from a normal male DNA sample. A similar process is carried out, analyzing DNA from 12 normal females. These values are similarly averaged, and they are used to provide N-ratios expected from normal female DNA.

As the next step in the analysis, the initial ratios (I-ratios) that were obtained against the internal standard from the unknown DNA being analyzed are each divided by the respective N-ratios for a person of the same gender to obtain a factor that is termed a conversion factor (C-factor). This procedure is used to calculate a C-factor for each of the probes. It is felt that each of these C-factors should be between about 1.25 and 0.75, and any C-factor that is outside this range is decreed to be abnormal and is excluded from subsequent analysis. After the C-factors have been calculated for each of the probes on the mircoarrays, except for the probe that represents the internal control gene, they are all averaged in order to provide an average C-factor (which of course will be between 0.75 and 1.25). Once this average C-factor has been established for one set of duplicate microarrays, each original average I-ratio that was first obtained is divided by this average C-factor to produce an adjusted ratio (A-ratio) for each. It has been found that this particular step is effective to reduce overall variability that might possibly result from the variation of the internal standard for any particular manufacturing run of microarrays; in this manner, the overall coefficient of variation is reduced by about 2-4%, which is considered to be significant.

Following this adjustment of the I-ratios by using the average C-factor to obtain the A-ratios, diagnosis is carried out for each probe using another rule which holds that any ratio value that deviates from the normal ratio value by more than 25% is an indication that the genomic DNA sample is abnormal for that particular targeted segment. For example, if the I-ratio of the signal of the probe that is indicative of chromosome 21 for a male sample to the internal standard used on the two duplicate microarrays was 1.01, and for this particular test procedure, the average C-factor was calculated to be 1.10, a readjustment for the chromosome 21 probe ratio would be figured as follows: 1.01/1.10 equals 0.92 (the A-ratio). Then the A-ratio (i.e., 0.92) would be compared to the N-ratio of the signal for the chromosome 21 probe for a normal male sample, which had earlier been found to be about 0.68. It can thus be seen that this value is about 35% higher than the normal ratio; thus, this sample would be diagnosed as being indicative of trisomy 21. As a matter of interest, the theoretical value for trisomy 21 is generally accepted to be about 1.02, which is reasonably close to the readjusted ratio of 0.92 that was obtained as a result of the analysis.

Analysis for the value obtained from each of the probes is carried out in the same manner, and as a result, it is possible to diagnose for the presence or absence of a chromosomal disorder with respect to each of these selected potential disorders in a single assay procedure. For example, where a trisomy disorder is detected, the intensity at the respective probe would be substantially higher, and when a microdeletion or other mutation is found, the intensity of the respective probe will be substantially lower. To authenticate this test procedure using the microarrays, testing has now been carried out using DNA having each of the 8 specific chromosomal disorders mentioned hereinbefore, and the test results obtained have demonstrated 100% sensitivity and 100% specificity with respect to 24 samples of DNA known to be normal and with respect to 48 different DNA samples known to contain specific abnormalities. Although only 8 potential chromosomal disorders have been tested to date, it is clear that other conditions of aneuloploidy and/or microdeletions can be readily included as a part of such a test being performed on a single microarray, and it is fully expected that similar detection and diagnosis will be obtained.

The following examples are presented to provide the best mode presently known for carrying out the invention using probes and sets of primers directed to as many as 9 different chromosomes, 8 of which are directed to potential disorders. However, it should be understood that these examples are presented for purposes for illustration only and is not considered to be in any way limiting upon the scope of this invention which is of course defined the by claims that appear at the end of hereof.

EXAMPLE 1

As one example of an assay procedure that might be employed to detect any one of chromosomal disorders resulting from aneuploidy or microdeletions with respect to eight different chromosomes, 10 ng of eukaryotic genomic DNA is obtained and routinely purified. Following purification, a multiplex PCR reaction is carried out using the formulation in Table 1:

TABLE 1

Volume of PCR Components

| Component | Amount (µL) |
|---|---|
| AmpliTaq Gold PCR Master Mix | 25 |
| Purified genomic DNA (UMB1839-M, 2 ng/µL) | 5 |
| Primer mix | 5 |
| DEPC water | 15 |
| Total | 50 |

A reaction chamber having a volume of about 50 microliters is employed. The pairs of primers, namely SEQ ID NO: 1 to SEQ ID NO: 18, in the primer mix are designed to flank targeted regions of the various chromosomes selected for investigation.

Concentrations in the primer mix (10×) ranged from 1.25 $_c$M to 2.5 $_c$M. The commercial PCR Master Mix includes appropriate amounts of deoxyribonucleoside substrates, appropriate enzymes, such as Taq, and buffers. The forward primers are 5-phosphorylated, and the reverse primers are covalently bonded to a fluorescent label, i.e., a cyanine (Cy-3). The mixture of all components was amplified using an ABI 9700 Thermocycler. The PCR cycle times and temperatures were as follows:

95° C. 11'; 96° C. 1'; 94° C. 30", 55° C. 30" and 70° C. 30" 10 cycles; 94° C. 30", 55° C. 30" and 70° C. 30" 13 cycles; 60° C. 10'.

Upon completion of the PCR amplification, the double-stranded, amplified material was purified with QIAquick PCR Purification Kit (Qiagen). The sense strand of the purified material was digested with Lambda Exonuclease (1.5 $_c$L, 5 units per $_c$L, New England BioLabs) for 30 minutes at 37° C.

The resulting labeled, single strand material was dissolved in a hybridization solution containing 3× SSC and 0.1% Triton X-100 and was divided into two equal aliquots. Each sample was hybridized to a 3D microarray to which 9 different probes, i.e., SEQ ID NO: 19 to SEQ ID NO: 27, were bound at discrete locations and incubated at 45° C. for 14 hours. Unbound targets were removed by washing for 15 minutes at 37° C. with a washing solution containing 1× SSC and 0.1% Triton X-100. Then they are washed one more time with 10 mM MgCl$_2$ and 5 mM Tris-HCl buffer at pH 8.0 for 15 seconds at room temperature. After drying, the fluorescence image of each hybridized 3D microarray (A and B) was obtained with a laser scanner (ScanArray® Lite, Perkin Elmer).

The image was analyzed with a rule-based algorithm as follows:

TABLE 2

Fluorescence Signal Intensity of the Two 3D microarrays
Laser power at 60
PMT gain at 85

| Gene | A | B |
|---|---|---|
| GAPD | 31,177 | 32,908 |
| Xp22 | 6,642 | 7,177 |

TABLE 2-continued

Fluorescence Signal Intensity of the Two 3D microarrays
Laser power at 60
PMT gain at 85

| Gene | A | B |
| --- | --- | --- |
| SRY | 5,286 | 5,334 |
| SOD1 | 31,223 | 33,624 |
| ATP7B | 21,703 | 23,202 |
| WDR7 | 9,119 | 9,325 |
| ELN | 10,201 | 10,498 |
| TAS2R1 | 9,650 | 9,825 |
| DGCR2 | 11,579 | 13,181 |

The ratio of the signal for each of the genes to the signal for GAPD is first computed. The results are shown in Table 3.

TABLE 3

Initial Ratios (I-ratios) of Individual Signals
Against Signal of Internal Standard GAPD

| Gene | A | B |
| --- | --- | --- |
| Xp22 | 0.21 | 0.22 |
| SRY | 0.17 | 0.16 |
| SOD1 | 1.00 | 1.02 |
| ATP7B | 0.70 | 0.71 |
| WDR7 | 0.29 | 0.28 |
| ELN | 0.33 | 0.32 |
| TAS2R1 | 0.31 | 0.30 |
| DGCR2 | 0.37 | 0.40 |

The average ratio and the % difference between the values for each gene are then computed.

TABLE 4

Average Ratio and % Difference Between the two 3D microarrays

| | Average ratio | % difference between two 3D microarrays |
| --- | --- | --- |
| Xp22 | 0.22 | 2 |
| SRY | 0.17 | 5 |
| SOD1 | 1.01 | 2 |
| ATP7B | 0.70 | 1 |
| WDR7 | 0.29 | 3 |
| ELN | 0.33 | 3 |
| TAS2R1 | 0.30 | 4 |
| DGCR2 | 0.39 | 8 |

In this sample, none of the % differences shows high variability.

TABLE 5

Conversion factor calculation and ratio
adjusted with an average C-factor

| Gene | Average ratio | N-ratios | C-factor | A-ratios |
| --- | --- | --- | --- | --- |
| Xp22 | 0.22 | 0.19 | 1.14 | 0.20 |
| SRY | 0.17 | 0.17 | 1.02 | 0.15 |
| SOD1 | 1.01 | 0.68 | | 0.92 |
| ATP7B | 0.70 | 0.59 | 1.20 | 0.63 |
| WDR7 | 0.29 | 0.26 | 1.13 | 0.26 |
| ELN | 0.33 | 0.35 | 0.96 | 0.30 |
| TAS2R1 | 0.30 | 0.25 | 1.18 | 0.27 |
| DGCR2 | 0.39 | 0.35 | 1.10 | 0.35 |
| Avg C-factor | | | 1.10 | |

In this sample, the A-ratios of all genes except SOD1 are within about 15% of the N-ratios, which means that the disorders represented by these genes are not present in the sample. The A-ratio for SOD1 is 0.92, which is 35% higher than 0.68 from the N-ratio. The magnitude of the percent difference indicates that the sample is one from a subject afflicted with Trisomy 21; moreover, the theoretical value for Trisomy 21 is 0.93. Because of the DNA tested was later indicated to have indeed that of a subject afflicted with Trisomy 21, the test is thus considered to validate the method of diagnosis using this kit.

EXAMPLE 2

As another example, a similar assay procedure to that described in Example 1 was carried out wherein primers and probes targeted to eight different chromosomes are employed. 10 ng of eukaryotic genomic DNA was obtained and routinely purified. Following purification, a multiplex PCR reaction was carried out using the same formulation as in Example 1.

A reaction chamber having a volume of about 50 microliters was employed. The same primer mix as used in Example 1 was employed, with the primer pairs being designed to flank targeted regions of the nine chromosomes to be investigated.

Concentrations in the primer mix ranged from 1.25 μM to 2.5 μM. The commercial PCR Master Mix included appropriate amounts of deoxyribonucleoside substrates, appropriate enzymes, such as Taq, and buffers. The forward primers were 5'-phosphorylated, and the reverse primers were covalently bonded to a fluorescent label, i.e., a cyanine (Cy-3).

PCR amplification, purification and digestion of the sense strands of the purified material were carried out as in Example 1.

The resulting labeled, single strand material was dissolved in hybridization solution containing 3× SSC and 0.1% Triton X-100 and was divided into two equal aliquots. Each sample was hybridized to a 3D microarray the same as used in Example 1 to which 9 different probes were bound at discrete locations by incubation at 45° C. for 14 hours. Unbound targets were removed by washing for 15 minutes at 37° C. with a washing solution containing 1× SSC and 0.1% Triton X-100. After drying, the fluorescence image of each hybridized 3D microarray (A and B) was obtained with a laser scanner (ScanArray® Lite, Perkin Elmer).

The image was analyzed with a rule-based algorithm as follows:

TABLE 6

Fluorescence Signal Intensity of the Two 3D microarrays
Laser power at 70
PMT gain at 85

| Gene | A | B |
| --- | --- | --- |
| GAPDH | 45,888 | 45,918 |
| XP22 | 15,407 | 16,675 |
| SRY | Background | Background |
| SOD1 | 30,392 | 32,665 |
| ATP7B | 26,406 | 25,668 |
| WDR7 | 10,193 | 10,014 |
| ELN | 17,115 | 15,766 |
| TAS2R1 | 9,938 | 10,210 |
| DGCR2 | 9,248 | 10,244 |

The ratio of the signal for each of the genes to the signal for GAPD is first computed. The results are shown in Table 7.

TABLE 7

Initial Ratios (I-ratios) of Individual Signals
Against Signal of Internal Standard GAPD

| Gene | A | B |
|---|---|---|
| XP22 | 0.34 | 0.36 |
| SRY | — | — |
| SOD1 | 0.66 | 0.71 |
| ATP7B | 0.58 | 0.56 |
| WDR7 | 0.22 | 0.22 |
| ELN | 0.37 | 0.34 |
| TAS2R1 | 0.22 | 0.22 |
| DGCR2 | 0.20 | 0.22 |

The average ratio and the % difference between the values for each gene are then computed.

TABLE 8

Average Ratio and % Difference Between the two 3D microarrays

| | Average ratio | % difference between two 3D HydroArrays |
|---|---|---|
| XP22 | 0.35 | 8 |
| SRY | — | — |
| SOD1 | 0.69 | 7 |
| ATP7B | 0.57 | 3 |
| WDR7 | 0.22 | 2 |
| ELN | 0.36 | 9 |
| TAS2R1 | 0.22 | 3 |
| DGCR2 | 0.21 | 11 |

In this sample, none of the % differences shows high variability.

TABLE 9

Conversion factor calculation and ratio adjusted with an average C-factor

| Gene | Average ratio | N-ratios | C-factor | A-ratios |
|---|---|---|---|---|
| XP22 | 0.35 | 0.35 | 1.00 | 0.35 |
| SRY | — | — | — | — |
| SOD1 | 0.69 | 0.65 | 1.06 | 0.70 |
| ATP7B | 0.57 | 0.56 | 1.02 | 0.57 |
| WDR7 | 0.22 | 0.25 | 0.89 | 0.22 |
| ELN | 0.36 | 0.33 | 1.07 | 0.36 |
| TAS2R1 | 0.22 | 0.25 | 0.88 | 0.22 |
| DGCR2 | 0.21 | 0.32 | | 0.22 |
| Avg C-factor | | | 0.99 | |

In this sample, the absence of the SRY gene shows the subject was a female (because of lack of a Y-chromosome); the A-ratios of all the remaining genes except DGCR2 are within about 12% of the N-ratios, which means that the disorders represented by these genes are not present in the sample. The A-ratio for DGCR2 is 0.22, which is 31% lower than 0.32 from the N-ratio. The magnitude of the percentage difference indicates that the sample is one from a subject afflicted with DiGeorge syndrome.

The DNA tested was later identified to have indeed been one from tissue of a female subject afflicted with DiGeorge syndrome; the test is thus considered to validate the method of diagnosis using this kit.

EXAMPLE 3

A 0.3 ng sample of the same DNA used in Example 1 is obtained, purified, amplified, digested and prepared for hybridization as set forth above in Example 1. However, in this procedure, assaying is carried out only for genes GAPD, XP22, SRY, FG9, WDR7, and SOD1. The sets of primers included in the primer mix are SEQ ID NO: 1 and 2; SEQ ID NO: 3 and 4; SEQ ID NO: 28 and 29; SEQ ID NO: 30 and 31; SEQ ID NO: 32 and 33; and SEQ ID NO: 34 and 35.

The resulting hybridization solution containing the appropriate buffers is again divided into two equal aliquots. Each aliquot is hybridized to a 3D microarray to which six different probes are bound at discrete locations; the probes employed are SEQ ID NO: 19 and 20 and SEQ ID NO: 36 to 39. Incubation is carried out as before, and unbound targets are removed by washing in the same manner. After drying, each microarray is scanned with the laser scanner used in Example 1 to obtain the fluorescence image thereof.

The results are analyzed using the rule-based algorithm in the same manner as set forth as in regard to Example 1. The results again are that the A-ratios for four of the genes are within 15% of the N-ratios; the exception is the A-ratio for SOD1. As a result, the testing using a 0.3 ng sample of the genomic DNA again diagnosed it as one of a subject afflicted with Trisomy 21 (Down's syndrome).

Although the invention has been described with regard to some preferred embodiments which constitute the best mode known at this time to the inventor for carrying out his invention, it should be understood the various changes and modifications as would be obvious to one of ordinary skill in this art may be made without departing from the scope of the invention which is set forth in the claims appended hereto. For example, although it is preferred to employ probes containing at least the entire sequences set forth herein, probes a major portion of the recited sequences may also be used if desired. The disclosures of all U.S. patents and applications and articles referenced are expressly incorporated herein by reference.

BRIEF DESCRIPTION OF THE SEQUENCE LISTING

SEQ ID NO 1 and SEQ ID NO 2 are primers for amplifying a 139 base pair segment of the human GAPD gene.

SEQ ID NO 3 and SEQ ID NO 4 are primers for amplifying a 158 base pair segment of the X-chromosome.

SEQ ID NO 5 and SEQ ID NO 6 are primers are for amplifying a 171 base pair segment of the human SRY gene.

SEQ ID NO 7 and SEQ ID NO 8 are primers for amplifying a 127 base pair segment of the ATP7B gene.

SEQ ID NO 9 and SEQ ID NO 10 are primers for amplifying a 151 base pair segment of the human WDR7 gene.

SEQ ID NO 11 and SEQ ID NO 12 are primers for amplifying a 124 base pair segment of the SOD1 gene.

SEQ ID NO 13 and SEQ ID NO 14 are primers for amplifying a 167 base pair segment of the human TAS2R1 gene.

SEQ ID NO 15 and SEQ ID NO 16 are primers for amplifying a 138 base pair segment of the ELN gene.

SEQ ID NO 17 and SEQ ID NO 18 are primers for amplifying a 145 base pair segment of the DGCR2 gene.

SEQ ID NO 19 through SEQ ID NO 27 are probe oligomers having a 5' end designed to attach to spots on a microarray plate and a 3' region capable of hybridizing to the respective amplified PCR product following digestion of one strand.

SEQ ID NO 28 and SEQ ID NO 29 are primers for amplifying a 175 base pair segment of the human SRY gene.

SEQ ID NO 30 and SEQ ID NO 31 are primers for amplifying a 139 base pair segment of the FGF9 gene.

SEQ ID NO 32 and SEQ ID NO 33 are primers for amplifying a 172 base pair segment of the human WDR7 gene.

SEQ ID NO 34 and SEQ ID NO 35 are primers for amplifying a 129 base pair segment of the SOD1 gene.

SEQ ID NO 36 through SEQ ID NO 39 are probe oligomers having a 5' end designed to attach to spots on a microarray plate and a 3' region capable of hybridizing to the respective amplified PCR product following digestion of one strand.

SEQ ID NO 40 and SEQ ID NO 41 are primers for amplifying a segment of the FGF9 gene.

SEQ ID NO 42 is probe oligomer having a 5' end designed to attach to spots on a microarray plate and a 3' region capable of hybridizing to the PCR-amplified segment of the FGF9 gene following digestion of one strand.

The invention claimed is:

1. A method for detecting any one of multiple chromosomal disorders in a single assay, which method comprises the steps of:

a. making a polymerase chain reaction (PCR) mixture by mixing in a vessel components comprising:

(i) eukaryotic genomic DNA;

(ii) a plurality of pairs of forward and reverse DNA primer oligonucleotides wherein one primer of each said pair is complementary to a 3' sequence of a targeted segment of a first DNA strand of the eukaryotic DNA and the other primer is complementary to the 3' sequence of the second strand of the targeted segment, the length of the segment of eukaryotic DNA being between about 50 and about 300 base pairs, wherein one of the primers of each pair has a detectable label attached to its 5' end, wherein of said plurality of different pairs of primers there are pairs targeted to a segments of a selected different chromosomes of interest, each of which is indicative of a potential chromosomal disorder, and wherein one pair is targeted for a segment of a single control gene which is present on a chromosome other than one on which there is a targeted segment and does not target any chromosome segment that might be indicative of a potential aneuploidy; and (iii) PCR buffers and enzymes necessary to carry out PCR amplification;

b. conducting a PCR for between about 5 and about 60 temperature cycles to create amplified PCR products;

c. purifying said products of step (b) and obtaining single-stranded DNA having the detectable labels, d. contacting a microarray with products of step (c), which microarray has a plurality of spots that each contain DNA oligonucleotide probes having nucleotide sequences complementary to a nucleotide sequence of one of said strands of each of said targeted segments;

e. hybridizing said DNA oligonucleotide probes and said PCR-amplified label-containing single-stranded products;

f. detecting the presence and relative quantity of the PCR-amplified products hybridized to the microarray by imaging the microarray; and g. diagnosing whether or not a chromosomal disorder exists with respect to one or more of said selected different chromosomes by comparing said imaging of the relevant spots on said microarray for each said targeted segment of a selected chromosome to the imaging of spots relevant to said control gene to determine a ratio of such intensities for each of a plurality of said targeted segments, termed an I-ratio, then dividing each said I-ratio by an N-ratio obtained from similar testing of multiple samples of genomic DNA of the same gender known to be normal to obtain a C-factor for each, averaging all said C-factors to obtain an average C-factor, then adjusting each said I-ratio by said average C-factor, and then comparing each said adjusted I-ratio to the respective N-ratio to determine if a disorder exists.

2. A method for detecting any one of a plurality of different chromosomal disorders in a single assay, which method comprises the steps of:
   a. making a polymerase chain reaction (PCR) mixture by mixing in a vessel components comprising:
      (i) eukaryotic genomic DNA;
      (ii) different pairs of forward and reverse DNA primer oligonucleotides designed to amplify each of a plurality of target segments wherein one primer of each said pair is complementary to a 3' sequence of a targeted segment of between about 100 and about 250 base pairs of a first eukaryotic DNA strand and the other primer is complementary to the 3' sequence of the second strand of the target segment, wherein one of the primers of each pair has a detectable label attached at the 5' end thereof, and wherein said different pairs of primers include a plurality of pairs that are targeted to selected segments of different chromosomes which are of interest from the standpoint of different potential chromosomal disorders and one pair that is targeted for a segment of a single control gene; and
      (iii) PCR buffers and enzymes necessary to carry out PCR amplification;
   b. conducting a PCR for between about 5 and about 60 temperature cycles to create amplified PCR products;
   c. purifying said amplified PCR products and obtaining single-stranded DNA having the labels by digestion of the sense strand of the amplified double-stranded PCR product;
   d. contacting a microarray with the resulting antisense products of step (c), which microarray has a plurality of spots that each contain DNA oligonucleotide probes having nucleotide sequences complementary to a nucleotide sequence of one of said label-carrying strands of said targeted segments;
   e. hybridizing said DNA oligonucleotide probes in said microarray and said PCR-amplified label-containing single-stranded products;
   f. detecting the presence and relative quantity of the PCR-amplified products hybridized to the microarray by imaging of the microarray; and
   g. diagnosing whether or not a chromosomal disorder exists with respect to one or more of said plurality of chromosomes of interest on which there were targeted segments by:
      (i) first comparing said imaging of relevant spots on said microarray for each said chromosome of interest to the imaging of spots relevant to said single control gene to obtain a plurality of I-ratios;
      (ii) comparing each of said plurality of I-ratios with the respective N-ratio that is average for normal DNA of persons of that gender to obtain a plurality of C-factors;
      (iii) obtaining an average C-factor from said plurality of individual C-factors by averaging all of said individual C-factors between 0.75 and 1.25;
      (iv) dividing each said I-ratio by said average C-factor to obtain an adjusted I-ratio (A-ratio) for each; and
      (v) then comparing each A-ratio for each of said plurality of chromosomes of interest to said respective N-ratio for that chromosome to determine the difference from normal.

3. The method according to claim 2 wherein at least two of the targeted segments of eukaryotic genomic DNA selected are associated with potential microdeletions of chromosomal DNA that would give rise to chromosomal disorders selected from the group consisting of:
   Williams-Beuren syndrome,
   Cri du chat syndrome, and
   DiGeorge syndrome.

4. The method according to claim 2 wherein at least two of the targeted segments are selected to detect chromosomal aberrations selected from the group consisting of trisomy 13, trisomy 18, trisomy 21 and X- and Y-chromosome anomaly.

5. The method according to claim 2 wherein said detectable labels are color-detectable labels.

6. The method according to claim 5 wherein said color-detectable labels are attached to the reverse primers and the forward primer of each pair has phosphate at its 5' end.

7. The method of claim 6 wherein said detectable labels are fluorescent dyes.

8. The method of claim 1 wherein the double-stranded product of step (b) is first purified and then the sense strands of the purified product are digested with an exonuclease to obtain the single-stranded labeled antisense strand in step (c).

9. The method of claim 2 wherein the control gene is GAPD.

10. The method of claim 2 wherein the sizes of the probes range from about 25 to about 60 nucleotides and the targeted segments are between about 100 and 200 base pairs long.

11. The method of claim 2 wherein two microarrays are used in parallel and the imaging results from both are compared as an initial check on the validity of the hybridizing and imaging steps.

* * * * *

SEQUENCE LISTING

```
<160> NUMBER OF SEQ ID NOS: 42

<210> SEQ ID NO 1
<211> LENGTH: 19
<212> TYPE: DNA
<213> ORGANISM: Artificial
<220> FEATURE:
<223> OTHER INFORMATION: Primer

<400> SEQUENCE: 1
tggtgaagca ggcgtcgga                                                19

<210> SEQ ID NO 2
<211> LENGTH: 22
<212> TYPE: DNA
<213> ORGANISM: Artificial
<220> FEATURE:
<223> OTHER INFORMATION: Primer

<400> SEQUENCE: 2
aagtggtcgt tgagggcaat gc                                            22

<210> SEQ ID NO 3
<211> LENGTH: 22
<212> TYPE: DNA
<213> ORGANISM: Artificial
<220> FEATURE:
<223> OTHER INFORMATION: Primer

<400> SEQUENCE: 3
caggagggcg tttctcaagg at                                            22

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
tccaagagga aatccccacc ct                                            22

<210> SEQ ID NO 5
<211> LENGTH: 22
<212> TYPE: DNA
<213> ORGANISM: Artificial
<220> FEATURE:
<223> OTHER INFORMATION: Primer

<400> SEQUENCE: 5
cgcattcatc gtgtggtctc gc                                            22

<210> SEQ ID NO 6
<211> LENGTH: 22
<212> TYPE: DNA
<213> ORGANISM: Artificial
<220> FEATURE:
```

<223> OTHER INFORMATION: Primer

<400> SEQUENCE: 6
ctgtgcctcc tggaagaatg gc                                          22

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
acatggtccc tgaggtcttc gg                                          22

<210> SEQ ID NO 8
<211> LENGTH: 22
<212> TYPE: DNA
<213> ORGANISM: Artificial
<220> FEATURE:
<223> OTHER INFORMATION: Primer

<400> SEQUENCE: 8
gctccattga aggcaaggtc cg                                          22

<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9
ccgccacgaa ggttgagaac aa                                          22

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
tcaaacatcg tccaccccag gg                                          22

<210> SEQ ID NO 11
<211> LENGTH: 22
<212> TYPE: DNA
<213> ORGANISM: Artificial
<220> FEATURE:
<223> OTHER INFORMATION: Primer

<400> SEQUENCE: 11
agcagatgac ttgggcaaag gt                                          22

<210> SEQ ID NO 12
<211> LENGTH: 22
<212> TYPE: DNA
<213> ORGANISM: Artificial
<220> FEATURE:
<223> OTHER INFORMATION: Primer

<400> SEQUENCE: 12
ggcctcagac tacatccaag gg                                          22

```
<210> SEQ ID NO 13
<211> LENGTH: 24
<212> TYPE: DNA
<213> ORGANISM: Artificial
<220> FEATURE:
<223> OTHER INFORMATION: Primer

<400> SEQUENCE: 13
tgttgctgag ttctcagtgc catt                                              24

<210> SEQ ID NO 14
<211> LENGTH: 24
<212> TYPE: DNA
<213> ORGANISM: Artificial
<220> FEATURE:
<223> OTHER INFORMATION: Probe

<400> SEQUENCE: 14
tcaggaagga caggatagac agca                                              24

<210> SEQ ID NO 15
<211> LENGTH: 22
<212> TYPE: DNA
<213> ORGANISM: Artificial
<220> FEATURE:
<223> OTHER INFORMATION: Primer

<400> SEQUENCE: 15
cgttggtgct actgcttggt gg                                                22

<210> SEQ ID NO 16
<211> LENGTH: 22
<212> TYPE: DNA
<213> ORGANISM: Artificial
<220> FEATURE:
<223> OTHER INFORMATION: Primer

<400> SEQUENCE: 16
cgctcccctc ttgtttcctt gc                                                22

<210> SEQ ID NO 17
<211> LENGTH: 21
<212> TYPE: DNA
<213> ORGANISM: Artificial
<220> FEATURE:
<223> OTHER INFORMATION: Primer

<400> SEQUENCE: 17
cccgtgaagt tccatgtgcc a                                                 21

<210> SEQ ID NO 18
<211> LENGTH: 22
<212> TYPE: DNA
<213> ORGANISM: Artificial
<220> FEATURE:
<223> OTHER INFORMATION: Primer

<400> SEQUENCE: 18
agattaagcg ggttctgtgc ga                                                22

<210> SEQ ID NO 19
<211> LENGTH: 45
<212> TYPE: DNA
<213> ORGANISM: Artificial
<220> FEATURE:
<223> OTHER INFORMATION: Probe
```

<400> SEQUENCE: 19
ctacactgag caccaggtgg tctcctctga cttcaacagc gacac          45

<210> SEQ ID NO 20
<211> LENGTH: 45
<212> TYPE: DNA
<213> ORGANISM: Artificial
<220> FEATURE:
<223> OTHER INFORMATION: Probe

<400> SEQUENCE: 20
ctcaaggata agagcgacac ggcctgacag tcactagtat tcatt          45

<210> SEQ ID NO 21
<211> LENGTH: 45
<212> TYPE: DNA
<213> ORGANISM: Artificial
<220> FEATURE:
<223> OTHER INFORMATION: Probe

<400> SEQUENCE: 21
tctagagaat cccagaatgc gaaactcaga gatcagcaag cagct          45

<210> SEQ ID NO 22
<211> LENGTH: 45
<212> TYPE: DNA
<213> ORGANISM: Artificial
<220> FEATURE:
<223> OTHER INFORMATION: Probe

<400> SEQUENCE: 22
ctgataagtg atgacggcct cttggttgct gagtgagact ttgac          45

<210> SEQ ID NO 23
<211> LENGTH: 45
<212> TYPE: DNA
<213> ORGANISM: Artificial
<220> FEATURE:
<223> OTHER INFORMATION: Probe

<400> SEQUENCE: 23
acgtattccg tctgcacagg caaccaaggc cagtagaaag ctatg          45

<210> SEQ ID NO 24
<211> LENGTH: 45
<212> TYPE: DNA
<213> ORGANISM: Artificial
<220> FEATURE:
<223> OTHER INFORMATION: Probe

<400> SEQUENCE: 24
caaaggtgga aatgaagaaa gtacaaagac aggaaacgct ggaag          45

<210> SEQ ID NO 25
<211> LENGTH: 44
<212> TYPE: DNA
<213> ORGANISM: Artificial
<220> FEATURE:
<223> OTHER INFORMATION: Probe

<400> SEQUENCE: 25
gctcttgatt ttctctctgg ggaggcacac ccggcaaatg agaa          44

<210> SEQ ID NO 26
<211> LENGTH: 44

```
<212> TYPE: DNA
<213> ORGANISM: Artificial
<220> FEATURE:
<223> OTHER INFORMATION: Probe

<400> SEQUENCE: 26
gaatgtaaac cctttgtaac cccatcccat gcccctccga ctcc                    44

<210> SEQ ID NO 27
<211> LENGTH: 46
<212> TYPE: DNA
<213> ORGANISM: Artificial
<220> FEATURE:
<223> OTHER INFORMATION: Probe

<400> SEQUENCE: 27
cagagacaca aacatacaaa ggaaagatcc agacattcaa cgtaga                  46

<210> SEQ ID NO 28
<211> LENGTH: 22
<212> TYPE: DNA
<213> ORGANISM: Artificial
<220> FEATURE:
<223> OTHER INFORMATION: Primer

<400> SEQUENCE: 28
tggctttcgt acagtcatcc ct                                            22

<210> SEQ ID NO 29
<211> LENGTH: 24
<212> TYPE: DNA
<213> ORGANISM: Artificial
<220> FEATURE:
<223> OTHER INFORMATION: Primer

<400> SEQUENCE: 29
cacagaaatt acaggccatg caca                                          24

<210> SEQ ID NO 30
<211> LENGTH: 34
<212> TYPE: DNA
<213> ORGANISM: Artificial
<220> FEATURE:
<223> OTHER INFORMATION: Primer

<400> SEQUENCE: 30
ctcatcaaac ctatataagc acgtggacac tgga                               34

<210> SEQ ID NO 31
<211> LENGTH: 35
<212> TYPE: DNA
<213> ORGANISM: Artificial
<220> FEATURE:
<223> OTHER INFORMATION: Primer

<400> SEQUENCE: 31
gggtccactg gtctaggtaa aaaatgtgtg aattt                              35

<210> SEQ ID NO 32
<211> LENGTH: 24
<212> TYPE: DNA
<213> ORGANISM: Artificial
<220> FEATURE:
<223> OTHER INFORMATION: Primer

<400> SEQUENCE: 32
```
tgcctcagtt tctagtcagc caat                          24

<210> SEQ ID NO 33
<211> LENGTH: 24
<212> TYPE: DNA
<213> ORGANISM: Artificial
<220> FEATURE:
<223> OTHER INFORMATION: Primer

<400> SEQUENCE: 33
aggtctttac cccaggcatt caca                          24

<210> SEQ ID NO 34
<211> LENGTH: 34
<212> TYPE: DNA
<213> ORGANISM: PRIMER

<400> SEQUENCE: 34
tttgggtatt gttgggagga ggtagtgatt actt               34

<210> SEQ ID NO 35
<211> LENGTH: 35
<212> TYPE: DNA
<213> ORGANISM: Artificial
<220> FEATURE:
<223> OTHER INFORMATION: Primer

<400> SEQUENCE: 35
tcctgtcttt gtactttctt catttccacc tttgc              35

<210> SEQ ID NO 36
<211> LENGTH: 45
<212> TYPE: DNA
<213> ORGANISM: Artificial
<220> FEATURE:
<223> OTHER INFORMATION: Probe

<400> SEQUENCE: 36
tcttcgcctt ccgacgaggt cgatacttat aattcgggta tttct   45

<210> SEQ ID NO 37
<211> LENGTH: 45
<212> TYPE: DNA
<213> ORGANISM: Artificial
<220> FEATURE:
<223> OTHER INFORMATION: Probe

<400> SEQUENCE: 37
gatactatgt tgcattaaat aaagatggga ccccgagaga aggga   45

<210> SEQ ID NO 38
<211> LENGTH: 45
<212> TYPE: DNA
<213> ORGANISM: Artificial
<220> FEATURE:
<223> OTHER INFORMATION: Probe

<400> SEQUENCE: 38
cagcccaaag ttatcttctt aaatttttta caggtccatg aaaaa   45

<210> SEQ ID NO 39
<211> LENGTH: 45
<212> TYPE: DNA
<213> ORGANISM: Artificial
<220> FEATURE:
<223> OTHER INFORMATION: Probe

<400> SEQUENCE: 39
cagcccaaag ttatcttctt aaatttttta caggtccatg aaaaa     45

<210> SEQ ID NO 40
<211> LENGTH: 24
<212> TYPE: DNA
<213> ORGANISM: Artificial
<220> FEATURE:
<223> OTHER INFORMATION: Primer

<400> SEQUENCE: 40
gattctcatg ggttggccag gata     24

<210> SEQ ID NO 41
<211> LENGTH: 24
<212> TYPE: DNA
<213> ORGANISM: Artificial
<220> FEATURE:
<223> OTHER INFORMATION: Primer

<400> SEQUENCE: 41
actccagagc tcaaagtaac ccac     24

<210> SEQ ID NO 42
<211> LENGTH: 44
<212> TYPE: DNA
<213> ORGANISM: Artificial
<220> FEATURE:
<223> OTHER INFORMATION: Probe

<400> SEQUENCE: 42
acatcttctg tctattgaaa ggcaacttac ggctgggcgt ggtg     44